US 6,548,685 B2

(12) United States Patent
Zell

(10) Patent No.: US 6,548,685 B2
(45) Date of Patent: Apr. 15, 2003

(54) PROCESS FOR PREPARING TANTALUM ALKOXIDES AND NIOBIUM ALKOXIDES

(75) Inventor: Friedrich Zell, Rheinfelden (DE)

(73) Assignee: H.C. Starck GmbH, Goslar (DE)

( * ) Notice: Subject to any disclaimer, the term of this patent is extended or adjusted under 35 U.S.C. 154(b) by 0 days.

(21) Appl. No.: 10/098,639

(22) Filed: Mar. 15, 2002

(65) Prior Publication Data

US 2002/0143200 A1 Oct. 3, 2002

(30) Foreign Application Priority Data

Mar. 19, 2001 (DE) .......................... 101 13 169

(51) Int. Cl.[7] .............................. C07F 9/00; B05D 3/12
(52) U.S. Cl. ...................... 556/42; 427/226; 427/241; 427/255.19; 427/255.3; 427/587; 427/593; 427/594; 423/592
(58) Field of Search .................. 556/42; 427/587, 427/593, 594, 255.19, 255.3, 241, 226; 423/592

(56) References Cited

U.S. PATENT DOCUMENTS 5,858,323 A * 1/1999 Boyle ........................ 423/593

5,919,963 A * 7/1999 Hochido et al. .............. 556/42

FOREIGN PATENT DOCUMENTS

EP 0 251 432 1/1988

OTHER PUBLICATIONS

J Chem. Soc. (month unavailable) 1956 pp. 2381–2384 Normal Alkoxides of Quinquevalent Niobium by D. C. Bradley, B. N. Chakravarti, and W. Wardlaw.

CIBA Basel Jan. 1962 pp. 3–8 Ueber Alkoxyde und Phenolate von Niob und Tantal, Dr. G. Danliker et al.

* cited by examiner

Primary Examiner—Porfirio Nazario-Gonzalez
(74) Attorney, Agent, or Firm—Godfried R. Akorli; Diderico van Eyl

(57) ABSTRACT

The invention relates to a process for preparing niobium(V) alkoxides and tantalum(V) alkoxides, in particular niobium (V) ethoxide and tantalum(V) ethoxide, by reacting $NbCl_5$ or $TaCl_5$ with an appropriate alcohol in the presence of ammonia, wherein $NbCl_5$ or $TaCl_5$ is dissolved at a temperature of from about 0° C. to −50° C. in the alcohol containing from about 5 to about 7 mol of ammonia per mol of $NbCl_5$ or $TaCl_5$ to be reacted.

13 Claims, No Drawings

PROCESS FOR PREPARING TANTALUM ALKOXIDES AND NIOBIUM ALKOXIDES

BACKGROUND

The present invention relates to a process for preparing tantalum alkoxides and niobium alkoxides and to their use.

Tantalum alkoxides and niobium alkoxides can be utilized for the deposition of corresponding metal layers by means of chemical vapor deposition (CVD) and are therefore valuable starting compounds for producing extremely resistant components which are employed, for example, in the electronics industry.

The preparation of tantalum alkoxides and niobium alkoxides starts out from the corresponding metal chlorides. Thus, the reaction of niobium(V) chloride ($NbCl_5$) with alcohol and ammonia was described as early as 1956 by D. C. Bradley, B. N. Chakravarti and W. Wardlaw (J. Chem. Soc., 1956, 2381–2384). The reaction is carried out in two steps. Firstly, the alcohol is reacted with a suspension of $NbCl_5$ in an organic solvent, for example, benzene, resulting in a vigorous reaction. An excess of ammonia is subsequently passed into the reaction mixture. This forms ammonium chloride which is separated off by filtration and the desired niobium alkoxide which is isolated by distillation.

A two-stage process has also been described for the preparation of tantalum alkoxides (G. Dändliker, "Über Alkoxyde und Phenolate von Niob und Tantal" CIBA Basle, 1962), with the alcohol firstly being reacted with tantalum (V) chloride in the presence of toluene. An excess of alcohol is used and the reaction proceeds according to the following equation:

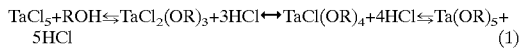

$$TaCl_5 + ROH \leftrightharpoons TaCl_2(OR)_3 + 3HCl \leftrightarrow TaCl(OR)_4 + 4HCl \leftrightharpoons Ta(OR)_5 + 5HCl \quad (1)$$

This is an equilibrium reaction in which the equilibrium can be shifted as a function of the HCl concentration. To obtain the desired product $Ta(OR)_5$, ammonia gas is passed into the reaction mixture in a second step. Here too, ammonium chloride formed is filtered off and the product is worked up by distillation. For example, tantalum(V) ethoxide is prepared by reaction of tantalum(V) chloride with ethanol in the presence of toluene at 50° C., with HCl being liberated. Ammonia gas is subsequently introduced, resulting in a rise in the reaction temperature to 64° C.

The processes described have the disadvantage that HCl gas is liberated, as a result of which an apparatus in which the reaction is carried out is subjected to severe corrosion. In addition, the reaction is carried out using large amounts of organic solvents which, in the preparation of niobium alkoxides and tantalum alkoxides on an industrial scale, have to be worked up or disposed of, which is costly. The reaction temperatures reported (50° C.) are significantly above the flash point of ethanol (12° C.), which is problematical from the point of view of safety.

It is therefore an object of the present invention to provide an efficient process for preparing niobium alkoxides and tantalum alkoxides which can be carried out without addition of organic solvents.

SUMMARY

The invention relates to a process for preparing a niobium (V) alkoxide or a tantalum(V) alkoxide of the formula (I)

$$M(OR)_5 \qquad (I),$$

wherein M represents Nb or Ta and R represents $C_1$–$C_5$-alkyl. The process comprises dissolving $NbCl_5$ or $TaCl_5$ in an alcohol of the formula (II)

$$ROH \qquad (II),$$

wherein R represents $C_1$–$C_5$-alkyl, at a temperature ranging from about 0° C. to about –50° C. under an inert atmosphere, wherein the alcohol contains from about 5 to about 7 mol of ammonia per mol of $NbCl_5$ or $TaCl_5$, and reacting $NbCl_5$ or $TaCl_5$ with alcohol of the formula (II), and thereby forming the niobium(V) alkoxide or the tantalum(V) alkoxide of the formula (I).

These and other features, aspects, and advantages of the present invention will become better understood with reference to the following description and appended claims.

DESCRIPTION

The invention provides a process for preparing niobium (V) alkoxides and tantalum(V) alkoxides of the formula (I)

$$M(OR)_5 \qquad (I),$$

where
  M represents Nb or Ta and
  R represents $C_1$–$C_5$-alkyl,
  by reacting $NbCl_5$ or $TaCl_5$ with an alcohol of the formula (II)

$$ROH \qquad (II),$$

where R is as defined above, in the presence of ammonia, which is characterized in that $NbCl_5$ or $TaCl_5$ is dissolved at a temperature of from about 0° C. to about –50° C. under an inert atmosphere in the alcohol of the formula (II) containing from about 5 to about 7 mol of ammonia per mol of $NbCl_5$ or $TaCl_5$ to be reacted.

The process of the invention is also suitable for preparing a mixture of niobium(V) alkoxides and tantalum(V) alkoxides of formula (I).

The process of the invention allows the preparation to be carried out without liberation of HCl gas and without use of large amounts of organic solvents. Furthermore, despite the fact that the reaction is carried out at a comparatively low temperature, it surprisingly enables the reaction time to be significantly reduced.

A particular advantage is that the process of the invention can be carried out without liberation of HCL gas. In one embodiment, the process liberates less than about 0.5 mole HCL gas per mole $NbCl_5$ or $TaCl_5$, preferably less than about 0.1 mole HCL gas, more preferably less than about 0.05 mole HCL gas. More preferably, the process according to the invention does not liberate any HCL gas.

Advantageously, as mentioned above, the process of the invention is carried out without use of large amounts of organic solvents. In one embodiment, less than about 0.1 mole of an organic solvent per mole of alcohol is used, preferably less than about 0.05 mole organic solvent is used, more preferably less than about 0.01 organic solvent is used. More preferably, the process according to the invention is carried out without use of any organic solvents other than the alcohol employed.

The process of the invention is particularly suitable for preparing niobium(V) alkoxides and tantalum(V) alkoxides of the formula (I) in which R preferably represents methyl, ethyl, n-propyl, i-propyl, n-butyl-, i-butyl or n-pentyl. R particularly preferably represents ethyl. M in the formula (I) preferably represents tantalum.

The preparation of the compounds niobium(V) chloride and tantalum(V) chloride used in the process of the invention is known to those skilled in the art. The preparation of $NbCl_5$ is, for example, described in J. Chem. Soc., 1956, p. 2383.

The reaction is preferably carried out at a temperature ranging from about −10° C. to about 45° C., particularly preferably at a temperature ranging from about −25° C. to about 40° C.

$NbCl_5$ or $TaCl_5$ is preferably reacted with an alcohol of the formula (II) containing from about 5.5 to about 6 mol of ammonia per mol of $NbCl_5$ or $TaCl_5$ to be reacted.

The alcohol containing the desired amount of ammonia can be prepared by passing a defined amount of dry ammonia into the appropriate amount of cooled alcohol with the aid of a glass frit.

Ammonia is preferably used in the form of ammonia gas having a purity of 99.9%. Relatively large traces of water in particular have an adverse effect on the desired reaction. It is therefore advantageous to dry the ammonia gas, for example, by passing the ammonia over solid sodium hydroxide, before it is passed into the alcohol.

It is advantageous to use from about 80 to about 90 moles of alcohol per mole of $NbCl_5$ or $TaCl_5$. It is possible to circulate unreacted alcohol. Preference is given to using alcohol having a water content of less than about 0.1 mol %.

Although the reaction of the invention is preferably carried out without addition of a further organic solvent, such an addition is nevertheless possible. An example of a suitable solvent is heptane.

The reaction is carried out in an inert atmosphere. For example, the reaction can be carried out in the presence of nitrogen or a noble gas.

The reaction mixture is preferably worked up by filtering off the ammonium chloride at a temperature ranging from about −25° C. to about −35° C., distilling the alcohol from the filtrate, filtering again at a temperature ranging from about 5° C. to about 0° C. and subsequently distilling the product under reduced pressure.

If tantalum(V) ethoxide is prepared by the process of the invention, it is advantageous to add small amounts, for example, about 1 per mil (0.1% by weight), of sodium methoxide after the second filtration at from about 5° C. to about 0° C. and to carry out a double distillation under reduced pressure.

Niobium and tantalum alkoxides prepared according to the invention can be used, for example, as starting compounds in chemical vapor deposition (CVD) processes.

Furthermore, the niobium and tantalum alkoxides prepared according to the invention can be employed in the preparation of catalysts, for the deposition of thin niobium oxide, tantalum oxide, niobium nitride or tantalum nitride films from solutions or for the deposition of homogeneous niobium or tantalum coatings by means of spin coating, dip coating or sol gel coating.

As such, in one embodiment, Applicants' is a process comprising subjecting, to a chemical vapor deposition process, a niobium(V) alkoxide or a tantalum(V) alkoxide of the formula (I) $M(OR)_5$ wherein the niobium(V) alkoxide or a tantalum(V) alkoxide of the formula (I) is prepared by dissolving $NbCl_5$ or $TaCl_5$ in an alcohol of the formula (II)

$$ROH \tag{II},$$

at a temperature ranging from about 0° C. to about −50° C., under an inert atmosphere, wherein the alcohol contains from about 5 to about 7 mol of ammonia per mol of $NbCl_5$ or $TaCl_5$, reacting $NbCl_5$ or $TaCl_5$ with alcohol of the formula (II), and thereby forming the niobium(V) alkoxide or the tantalum(V) alkoxide of the formula (I).

In another embodiment, Applicants invention is a process comprising depositioning, to a substrate, a niobium(V) alkoxide or a tantalum(V) alkoxide of the formula (I) $M(OR)_5$ (I), wherein M represents Nb or Ta and R represents $C_1$–$C_5$-alkyl; wherein the niobium(V) alkoxide or a tantalum (V) alkoxide of the formula (I) is prepared by dissolving $NbCl_5$ or $TaCl_5$ in an alcohol of the formula (II)

$$ROH \tag{II},$$

wherein R represents $C_1$–$C_5$-alkyl, at a temperature ranging from about 0° C. to about −50° C., under an inert atmosphere, wherein the alcohol contains from about 5 to about 7 mol of ammonia per mol of $NbCl_5$ or $TaCl_5$, reacting $NbCl_5$ or $TaCl_5$ with alcohol of the formula (II), and thereby forming the niobium(V) alkoxide or the tantalum(V) alkoxide of the formula (I).

In another embodiment, Applicants' invention is a process comprising depositioning (by spin coating, dip coating or sol gel coating) a niobium(V) alkoxide or a tantalum(V) alkoxide of the formula (I)

$$M(OR)_5 \tag{I},$$

wherein M represents Nb or Ta andR represents $C_1$–$C_5$-alkyl; to a substrate and forming a film selected from the group consisting of niobium oxide films, tantalum oxide films, niobium nitride films from a solution, wherein the niobium(V) alkoxide or a tantalum(V) alkoxide of the formula (I) is prepared by dissolving $NbCl_5$ or $TaCl_5$ in an alcohol of the formula (II)

$$ROH \tag{II},$$

wherein R represents $C_1$–$C_5$-alkyl, at a temperature ranging from about 0° C. to about −50° C., under an inert atmosphere, wherein the alcohol contains from about 5 to about 7 mol of ammonia per mol of $NbCl_5$ or $TaCl_5$, reacting $NbCl_5$ or $TaCl_5$ with alcohol of the formula (II), and thereby forming the niobium(V) alkoxide or the tantalum(V) alkoxide of the formula (i).

The process of the invention is illustrated by the examples below, but without the examples implying a restriction of the scope of the invention. All parts and percentages are by weight unless otherwise indicated.

EXAMPLES

Example 1

Preparation of tantalum(V) ethoxide 1 mol of high-purity tantalum(V) chloride (358 grams) were cooled to −40° C. A solution of 5.5 mol of dry ammonia (94 grams) in 80 mol of absolute ethanol (3,686 grams) was cooled to −40° C. The tantalum(V) chloride was added under a nitrogen atmosphere to the ammoniacal ethanol within 15 seconds while stirring vigorously (500 revolutions per minute (rpm)).

The resulting suspension was warmed to 5° C. during this addition and was subsequently cooled down to −40° C. again.

Ammonium chloride was formed and was separated off at −40° C. via a filter paper having a large pore size (about 0.005 mm). The filter cake was washed with 2 mol of ethanol (92 grams) at −40° C., added a little at a time. The filter cake consisted of 4.5 mol of ammonium chloride (241 grams) and 0.5 mol of ethanol (24 grams).

The filtrate was freed of the ethanol at 100° C. at atmospheric pressure on a rotary evaporator. 76 mol of ethanol (3501 grams) containing about 0.5 mol of ammonia (9 grams) were obtained as distillate. The ethanol recovered in this way was recirculated.

The distillation bottoms were cooled to 0° C. and the further ammonium chloride which precipitated was separated off via a filter paper having a large pore size (about 0.005 mm). In this filtration, 0.4 mol of ammonium chloride (18 grams) together with 0.1 mol of adhering tantalum(V) ethoxide (41 grams) were separated off. The product-containing filter cake was recirculated by introducing it quantitatively into the first precipitation step of a subsequent batch.

The filtrate was vacuum-distilled at 150° C. and 0.5 mbar via a Vigreux column having a length of about 0.5 m. This gave 0.8 mol of tantalum(V) ethoxide (325 grams). The distillation residue comprised a mixture of 0.1 mol of ammonium chloride (5 grams) and 0.1 mol of tantalum(V) ethoxide (41 grams), with the latter being present as a mixture of tantalum(V) ethoxide and tantalum oxide.

The yield was 80% of theory. It could be increased to 90% of theory by reuse of the filter cake from the second ammonium chloride precipitation.

To reduce the chloride content of the tantalum(V) ethoxide obtained, about 1 per mil (0.1% by weight) of sodium methoxide was added to it and it was then subjected to another vacuum distillation. The chloride content could be reduced from 200 ppm to <10 ppm in this way.

Example 2

Preparation of niobium(V) ethoxide 1 mol of high-purity niobium(V) chloride (270 grams) was cooled to −40° C. A solution of 5.5 mol of dry ammonia (94 grams) in 80 mol of absolute ethanol (3686 grams) was cooled to −40° C. The niobium(V) chloride was added under a nitrogen atmosphere to the ammoniacal ethanol within 15 seconds while stirring vigorously (500 rpm).

The resulting suspension was warmed to 5° C. during this addition and was subsequently cooled down to −40° C. again. Cooling was in each case carried out overnight in a laboratory freezer chest.

Ammonium chloride was formed and was separated off at −40° C. via a filter paper having a large pore size (about 0.005 mm). The filter cake was washed with 2 mol of ethanol (92 grams) at −40° C., added a little at a time. The filter cake consisted of 4.5 mol of ammonium chloride (241 grams) and 0.5 mol of ethanol (24 grams).

The filtrate was freed of the ethanol at 100° C. at atmospheric pressure on a rotary evaporator. 76 mol of ethanol (3501 grams) containing about 0.5 mol of ammonia (9 grams) were obtained as distillate. The ethanol recovered in this way was recirculated.

The distillation bottoms were cooled to 0° C. and the further ammonium chloride which precipitated was separated off via a filter paper having a large pore size (about 0.005 mm). In this filtration, 0.4 mol of ammonium chloride (18 grams) together with 0.1 mol of adhering niobium(V) ethoxide (32 grams) were separated off. The product-containing filter cake was recirculated by introducing it quantitatively into the first precipitation step of a subsequent batch.

The filtrate was vacuum-distilled at 140° C. and 0.5 mbar via a Vigreux column having a length of about 0.5 m. This gave 0.8 mol of niobium(V) ethoxide (255 grams). The distillation residue comprised a mixture of 0.1 mol of ammonium chloride (5 grams) and 0.1 mol of niobium(V) ethoxide (32 grams), with the latter being present as a mixture of niobium(V) ethoxide and niobium oxide.

The yield was 80% of theory. It could be increased to 90% of theory by reuse of the filter cake from the second ammonium chloride precipitation.

To reduce the chloride content of the niobium(V) ethoxide obtained, about 1 per mil (0.1% by weight) of sodium methoxide was added to it and it was then subjected to another vacuum distillation. The chloride content could be reduced from 200 ppm to <10 ppm in this way.

Although the present invention has been described in detail with reference to certain preferred versions thereof, other variations are possible. Therefore, the spirit and scope of the appended claims should not be limited to the description of the versions contained therein.

What is claimed is:

1. A process for preparing a niobium(V) alkoxide or a tantalum(V) alkoxide of the formula (I)

$$M(OR)_5 \qquad (I),$$

wherein

M represents Nb or Ta and

R represents $C_1$–$C_5$-alkyl;

the process comprising
dissolving $NbCl_5$ or $TaCl_5$ in an alcohol of the formula (II)

$$ROH \qquad (II),$$

wherein R represents $C_1$–$C_5$-alkyl, at a temperature ranging from about 0° C. to about −50° C. under an inert atmosphere, and wherein the alcohol contains from about 5 to about 7 mol of ammonia per mol of $NbCl_5$ or $TaCl_5$, reacting $NbCl_5$ or $TaCl_5$ with alcohol of the formula (II), and thereby forming the niobium(V) alkoxide or the tantalum (V) alkoxide of the formula (I).

2. The process according to claim 1, wherein R represents methyl, ethyl, n-propyl, i-propyl, n-butyl-, i-butyl or n-pentyl.

3. The process according to claim 1, wherein R represents ethyl.

4. The process according to claim 1, wherein the reaction is carried out at a temperature ranging from about −10° C. to about −45° C.

5. The process according to claim 1, wherein the reaction is carried out at a temperature ranging from about −25° C. to about −40° C.

6. The process according to claim 1, wherein the alcohol of the formula (II) contains from about 5.5 to about 6 mol of ammonia per mol of $NbCl_5$ or $TaCl_5$.

7. The process according to claim 1, wherein from about 80 to about 90 mol of alcohol are used per mol of $NbCl_5$ or $TaCl_5$.

8. The process according to claim 1, wherein the reaction mixture is worked up by filtering off the ammonium chloride at a temperature ranging from about −25° C. to about −35° C., distilling the alcohol from the filtrate, filtering again at a temperature ranging from about 5° C. to about 0° C. and subsequently distilling the product under reduced pressure.

9. The process of claim 1, wherein HCL gas is not liberated during the process.

10. A process comprising subjecting a niobium(V) alkoxide or a tantalum(V) alkoxide of the formula (I) $M(OR)_5$(I), wherein M represents Nb or Ta and R represents $C_1$–$C_5$-alkyl; to a chemical vapor deposition process;

wherein the niobium(V) alkoxide or a tantalum(V) alkoxide of the formula (I) has been prepared by dissolving $NbCl_5$ or $TaCl_5$ in an alcohol of the formula (II)

$$ROH \qquad (II),$$

wherein R represents $C_1$–$C_5$-alkyl, at a temperature ranging from about 0° C. to about −50° C., under an inert atmosphere, wherein the alcohol contains from about 5 to about 7 mol of ammonia per mol of $NbCl_5$ or $TaCl_5$, reacting $NbCl_5$ or $TaCl_5$ with alcohol of the formula (II), and thereby forming the niobium(V) alkoxide or the tantalum(V) alkoxide of the formula (I).

11. A process comprising depositioning, a niobium(V) alkoxide or a tantalum(V) alkoxide of the formula (I) $M(OR)_5$(I), wherein M represents Nb or Ta and R represents $C_1$–$C_5$-alkyl; to a substrate;

wherein the niobium(V) alkoxide or a tantalum(V) alkoxide of the formula (I) has been prepared by dissolving $NbCl_5$ or $TaCl_5$ in an alcohol of the formula (II)

$$ROH \qquad (II),$$

wherein R represents $C_1$–$C_5$-alkyl, at a temperature ranging from about 0° C. to about −50° C., under an inert atmosphere, wherein the alcohol contains from about 5 to about 7 mol of ammonia per mol of $NbCl_5$ or $TaCl_5$, reacting $NbCl_5$ or $TaCl_5$ with alcohol of the formula (II), and thereby forming the niobium(V) alkoxide or the tantalum(V) alkoxide of the formula (I).

12. A process comprising depositioning a niobium(V) alkoxide or a tantalum(V) alkoxide of the formula (I)

$$M(OR)_5 \qquad (I),$$

wherein M represents Nb or Ta and R represents $C_1$–$C_5$-alkyl; to a substrate and forming a film selected from the group consisting of niobium oxide films, tantalum oxide films, niobium nitride films from a solution, wherein the niobium(V) alkoxide or a tantalum(V) alkoxide of the formula (I) has been prepared by dissolving $NbCl_5$ or $TaCl_5$ in an alcohol of the formula (II)

$$ROH \qquad (II),$$

wherein R represents $C_1$–$C_5$-alkyl, at a temperature ranging from about 0° C. to about −50° C., under an inert atmosphere, wherein the alcohol contains from about 5 to about 7 mol of ammonia per mol of $NbCl_5$ or $TaCl_5$, reacting $NbCl_5$ or $TaCl_5$ with alcohol of the formula (II), and thereby forming the niobium(V) alkoxide or the tantalum(V) alkoxide of the formula (I).

13. The process of claim 11, wherein depositioning takes place by spin coating, dip coating or sol gel coating.

* * * * *